(12) United States Patent
Huy

(10) Patent No.: US 8,955,185 B2
(45) Date of Patent: Feb. 17, 2015

(54) DIRECT DRIVE ELECTRIC TOOTHBRUSH

(75) Inventor: Gerhart P. Huy, Hamilton Square, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 399 days.

(21) Appl. No.: 12/681,465

(22) PCT Filed: Oct. 3, 2008

(86) PCT No.: PCT/US2008/078758
§ 371 (c)(1),
(2), (4) Date: Jun. 18, 2010

(87) PCT Pub. No.: WO2009/046304
PCT Pub. Date: Apr. 9, 2009

(65) Prior Publication Data
US 2010/0282274 A1    Nov. 11, 2010

Related U.S. Application Data

(60) Provisional application No. 60/997,708, filed on Oct. 3, 2007.

(51) Int. Cl.
*A61C 17/16* (2006.01)
*A61C 17/34* (2006.01)
(52) U.S. Cl.
CPC .................................. *A61C 17/3427* (2013.01)
USPC .......................................................... 15/22.1
(58) Field of Classification Search
USPC ........................................... 15/22.1, 22.2, 28

IPC ............ A64B 13/02; A61C 17/22, 17/24, 17/26, A61C 17/32, 17/34

See application file for complete search history.

(56) References Cited

U.S. PATENT DOCUMENTS

| 5,072,482 | A | * | 12/1991 | Bojar et al. .................... 15/180 |
| 5,259,083 | A | * | 11/1993 | Stansbury, Jr. ................ 15/22.1 |
| 5,625,916 | A | | 5/1997 | McDougall |
| 5,732,432 | A | | 3/1998 | Hui |
| 5,784,743 | A | * | 7/1998 | Shek ............................... 15/22.1 |
| 5,836,030 | A | * | 11/1998 | Hazeu et al. .................... 15/22.1 |
| 6,347,425 | B1 | | 2/2002 | Fattori et al. |
| 6,536,066 | B2 | | 3/2003 | Dickie |
| 6,574,820 | B1 | | 6/2003 | Depuydt et al. |
| 6,725,490 | B2 | * | 4/2004 | Blaustein et al. ............... 15/22.2 |
| 6,735,803 | B2 | * | 5/2004 | Kuo ................................. 15/22.1 |
| 6,760,946 | B2 | | 7/2004 | Depuydt |
| 6,813,793 | B2 | | 11/2004 | Eliav |

(Continued)

*Primary Examiner* — Rachel Steitz
*Assistant Examiner* — Jennifer Gill
(74) *Attorney, Agent, or Firm* — Ware, Fressola, Maguire & Barber LLP; Keith Obert

(57) ABSTRACT

An electric toothbrush has an axially elongated body having a handle defining a hollow interior region for holding a motor disposed therein, a head comprising a static bristle holder plate having tufts of bristles disposed thereon and an oscillatory head bristle holder with other tufts of bristles disposed thereon. One end of the drive shaft is connected to the motor and an opposite end to a cam for directly driving the cam which has at least one lobe a portion of which cam is received in an oscillatory cavity for imparting a pushing force on the walls of the oscillatory cavity in response to rotation of the drive shaft for moving the oscillatory head bristle holder with a back and forth oscillatory motion. By eliminating the need for precision gearing, this direct drive arrangement simplifies and makes more efficient the translation of rotary motion into oscillatory motion.

14 Claims, 11 Drawing Sheets

(56) References Cited

U.S. PATENT DOCUMENTS

| | | | |
|---|---|---|---|
| 6,889,401 B2 | 5/2005 | Fattori et al. | |
| 6,892,412 B2 | 5/2005 | Gatzemeyer et al. | |
| 6,938,294 B2 | 9/2005 | Fattori et al. | |
| 6,944,901 B2 | 9/2005 | Gatzemeyer et al. | |
| 6,983,507 B2 | 1/2006 | McDougall | |
| 7,007,332 B2 | 3/2006 | Hohlbein | |
| 7,117,555 B2 | 10/2006 | Fattori et al. | |
| 7,162,764 B2* | 1/2007 | Drossler et al. | 15/22.1 |
| 7,185,383 B2 | 3/2007 | Gatzemeyer et al. | |
| 7,225,494 B2* | 6/2007 | Chan et al. | 15/22.1 |
| 7,266,855 B2* | 9/2007 | Zhuan | 15/22.4 |
| 7,310,844 B1* | 12/2007 | Rehkemper | 15/22.1 |
| 2003/0033679 A1* | 2/2003 | Fattori et al. | 15/22.1 |
| 2003/0079304 A1* | 5/2003 | Dworzan | 15/22.1 |
| 2003/0097723 A1* | 5/2003 | Li | 15/22.1 |
| 2003/0131427 A1 | 7/2003 | Hilscher et al. | |
| 2003/0140436 A1* | 7/2003 | Gatzemeyer et al. | 15/22.1 |
| 2003/0182746 A1* | 10/2003 | Fattori et al. | 15/22.1 |
| 2005/0050659 A1* | 3/2005 | Chan et al. | 15/22.1 |
| 2005/0125919 A1 | 6/2005 | Fattori | |
| 2005/0132513 A1 | 6/2005 | Eliav et al. | |
| 2006/0005331 A1* | 1/2006 | Schutz | 15/22.1 |
| 2006/0010623 A1* | 1/2006 | Crossman et al. | 15/22.1 |
| 2006/0019097 A1 | 1/2006 | Weihrauch | |
| 2006/0048315 A1* | 3/2006 | Chan et al. | 15/22.1 |
| 2006/0174431 A1* | 8/2006 | Nanda | 15/22.1 |
| 2006/0254006 A1* | 11/2006 | Blaustein et al. | 15/22.2 |
| 2007/0084002 A1* | 4/2007 | Drossler et al. | 15/22.1 |
| 2007/0251033 A1* | 11/2007 | Brown et al. | 15/22.1 |
| 2008/0115300 A1* | 5/2008 | Spooner et al. | 15/22.1 |
| 2011/0016647 A1* | 1/2011 | Biro et al. | 15/22.1 |

\* cited by examiner

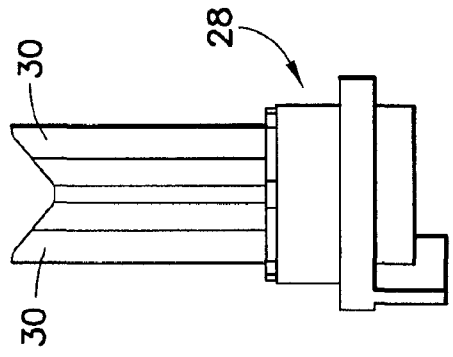
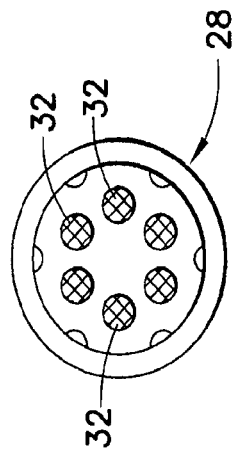
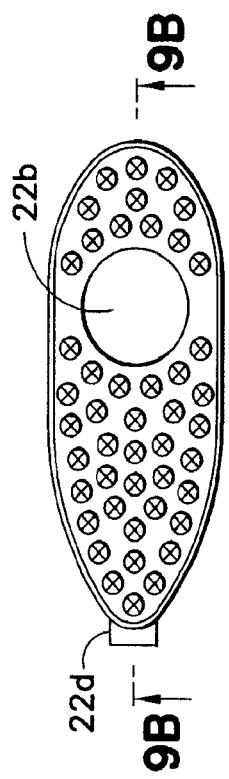
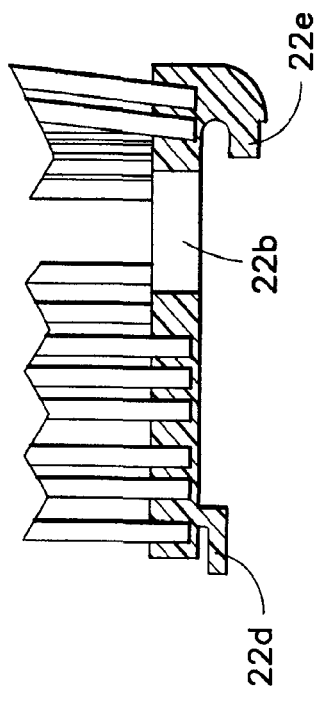

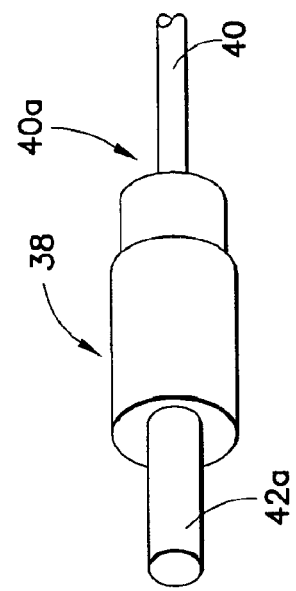
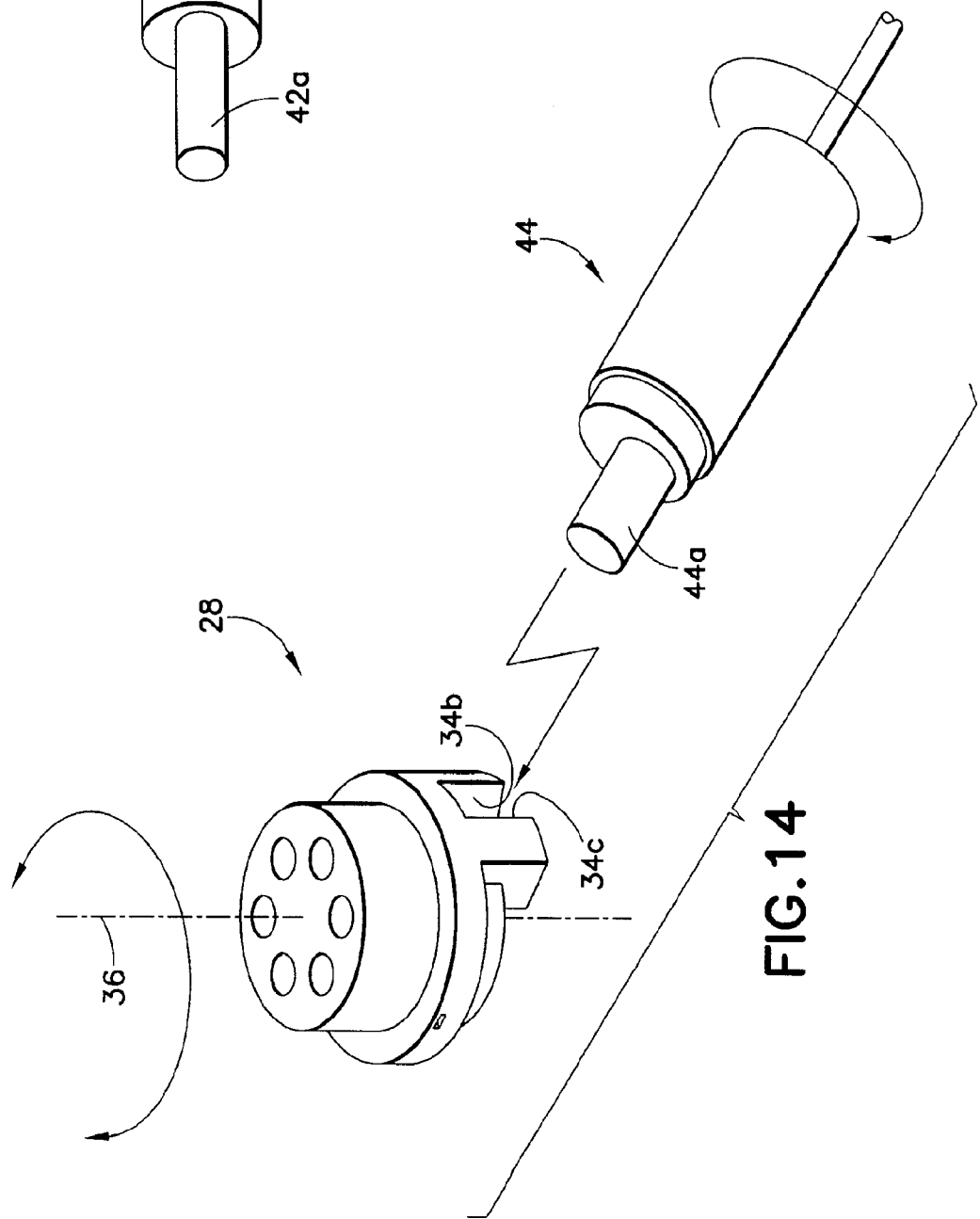

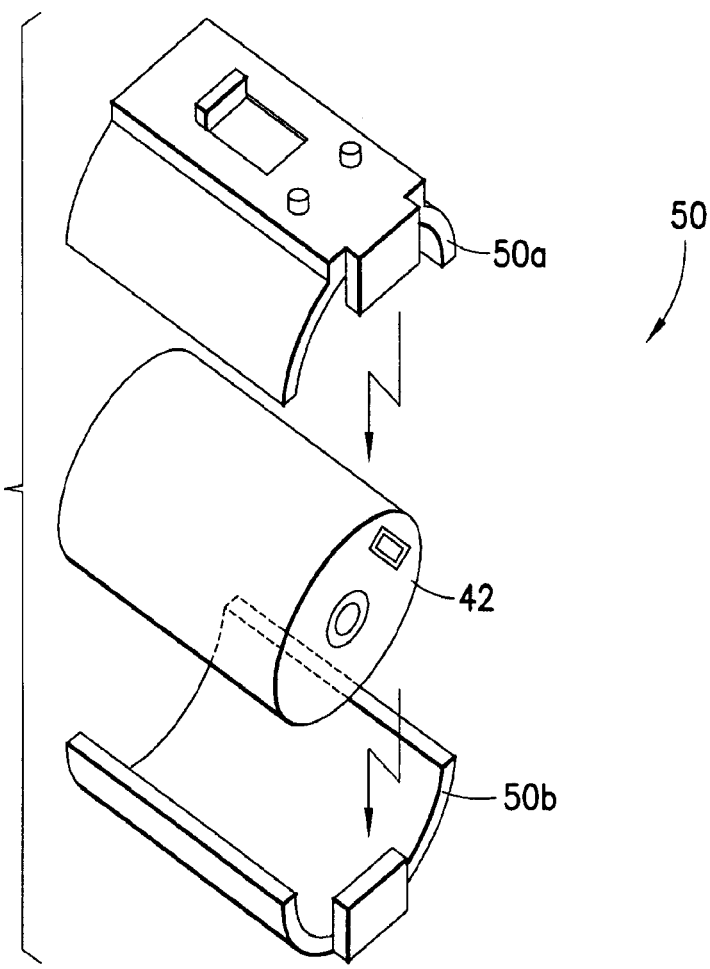

DIRECT DRIVE ELECTRIC TOOTHBRUSH

CROSS REFERENCE TO RELATED APPLICATION

This application claims the benefit of U.S. Provisional Application No. 60/997,708 filed Oct. 3, 2007.

TECHNICAL FIELD OF THE INVENTION

The present invention relates to the field of toothbrushes, and more particularly, the invention relates to the field of electrically powered toothbrushes.

BACKGROUND

Toothbrushes have traditionally utilized one or more groups of bristles that are fixed or otherwise attached to the head or end of the toothbrush. Toothbrushes are also known to utilize movable bristle sets or bristle holders that are mechanically or electrically powered. Generally, a significant cleaning efficacy results from a toothbrush that utilizes a combination of fixed bristles and moveable bristles. Typically, for example, an electrical motor and drive mechanism are retained within the body of the toothbrush and are coupled to the movable bristle sets or bristle holders. Upon activation of the motor and drive mechanism, the bristle holders may undergo a variety of different types of motion. Further, typically for example one or more batteries are also provided within the body of the toothbrush to power the drive mechanism and impart motion to the bristle holder.

The mechanisms used to impart motion to the bristle holders often utilize complicated, expensive and in many instances precision gearing mechanisms to move the bristle holder with a desired motion.

What is needed therefore is an electric toothbrush with a combination of fixed bristles and movable bristles that provides motion to a movable bristle holder without complicated, expensive and precision gearing mechanisms.

SUMMARY

In accordance with a first broad aspect of the invention an apparatus is presented and comprises a housing having a hollow interior, a motor, a drive shaft with an attached cam, the cam having a cam lobe, a fixed bristle plate, and an oscillating bristle plate. The cam is inserted into a cavity in the oscillating plate wherein the oscillating bristle plate oscillates through the action of the cam lobe upon the oscillating bristle plate. In some embodiments of the invention a collection of fixed bristles are attached to the fixed bristle plate. In some embodiments of the invention a collection of oscillating bristles are attached to the oscillating plate. In some embodiments of the invention the drive shaft is a straight drive shaft that extends the length of the apparatus from the motor to the cam. In some embodiments of the invention the cam pushes the oscillating plate back and forth up to 20 degrees in each direction from an at rest position. In some embodiments of the invention the cam is made of a material selected from the group consisting of metals and plastic. In some embodiments of the invention the drive shaft comprises a cylindrical bearing and a metal shaft attached to the anterior of the bearing. In some embodiments of the invention the bearing has one or more cruciform cross sectional regions. In some embodiments of the invention the bearing connects to the motor drive shaft by means of attachment. In some embodiments of the invention the means of attachment comprises a cored out region of the bearing suitable for press fitting the drive shaft directly onto the motor drive shaft. In some embodiments of the invention the diameter of the bearing varies as a function of the inner diameter of the hollow interior of the housing. In some embodiments of the invention the apparatus comprises an electric toothbrush.

In accordance with a second broad aspect of the invention, an electric toothbrush is presented and has an axially elongated body having a handle defining a hollow interior region shaped and configured for holding a motor disposed therein, a head comprising a static bristle holder plate and a movable oscillatory head bristle holder, said movable oscillatory head bristle holder being arranged and located on the static bristle holder plate so that the surface of the static bristle holder plate and the surface of the oscillatory head bristle holder lie in a common plane, a neck extending between the handle and the head, a drive shaft defining a longitudinal axis and configured for operatively connecting one end of the drive shaft to the motor and an opposite end to a cam having at least one lobe, and the movable oscillatory head bristle holder having a suitably sized and shaped cavity for receiving at least a portion of the cam such that the cam lobe imparts a pushing force on a first side wall of the cavity in response to rotation of the drive shaft, the oscillatory head bristle holder being responsive thereto for rotation in a first direction, and a pushing force on a second wall of the cavity opposite the first wall in response to rotation of the drive shaft, the oscillatory head bristle holder being responsive thereto for rotation in a second direction opposite to the first direction. In some embodiments of the invention the fixed bristle holder plate has tufts of bristles disposed thereon in a desired pattern. In some embodiments of the invention the movable oscillatory head bristle holder has tufts of other bristles disposed thereon. In some embodiments of the invention the tufts of other bristles of the movable oscillatory head bristle holder are at least partially surrounded by the tufts of bristles of the fixed static bristle holder plate. In some embodiments of the invention the static bristle holder plate is detachable.

BRIEF DESCRIPTION OF THE DRAWINGS

The foregoing and other features and benefits of the invention will become readily apparent from the following written description of exemplary embodiments taken in conjunction with the drawing figures wherein:

FIG. 9A is a top plan view showing tufts of bristles arranged to fully cover the front surface of the bristle holder plate according to some embodiments of the invention.

FIG. 9B is a cross-section view taken along the line 9B-9B of FIG. 9A showing the lugs and opening in which the oscillating head bristle carrier rotates according to some embodiments of the invention.

FIG. 10A is a side view showing tufts of bristles extending from the front surface an oscillating head bristle carrier according to some embodiments of the invention.

FIG. 10B is a top plan view showing an arrangement of tufts of bristles carried on the front surface of the oscillating head bristle carrier according to some embodiments of the invention.

FIG. 13 is a fragmentary perspective view of the coupler between the motor output drive shaft and the oscillatory head drive shaft according to some embodiments of the invention.

FIG. 14 is a schematic perspective exploded view showing the rotation of the cam lobe in the oscillating cavity driving the oscillating head bristle holder according to some embodiments of the invention.

FIG. 15 is an exploded perspective view showing the motor sandwiched between the top and bottom motor mounts according to some embodiments of the invention.

DETAILED DESCRIPTION

According to some embodiments, the present invention provides a way for the problem of how to drive an oscillating bristle carrier without complicated, expensive and often precision gearing mechanisms. The problem is solved according to some embodiments of the present invention by use of a novel plastic cam attached to a drive shaft which simplifies and makes more efficient the translation of rotary motion provided by the drive shaft into oscillatory motion in the tufted oscillating head. In the following written description like reference numbers refer to like parts.

Figure 1:
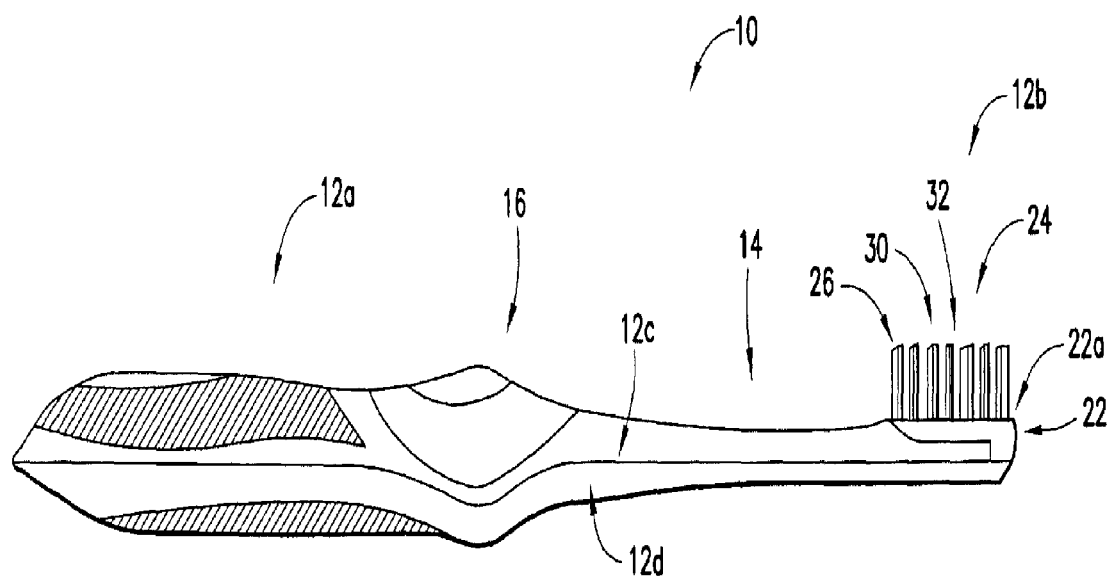
FIG. 1 shows a side view of an example of a direct drive electric toothbrush according to some embodiments of the invention.
Figure 4A:
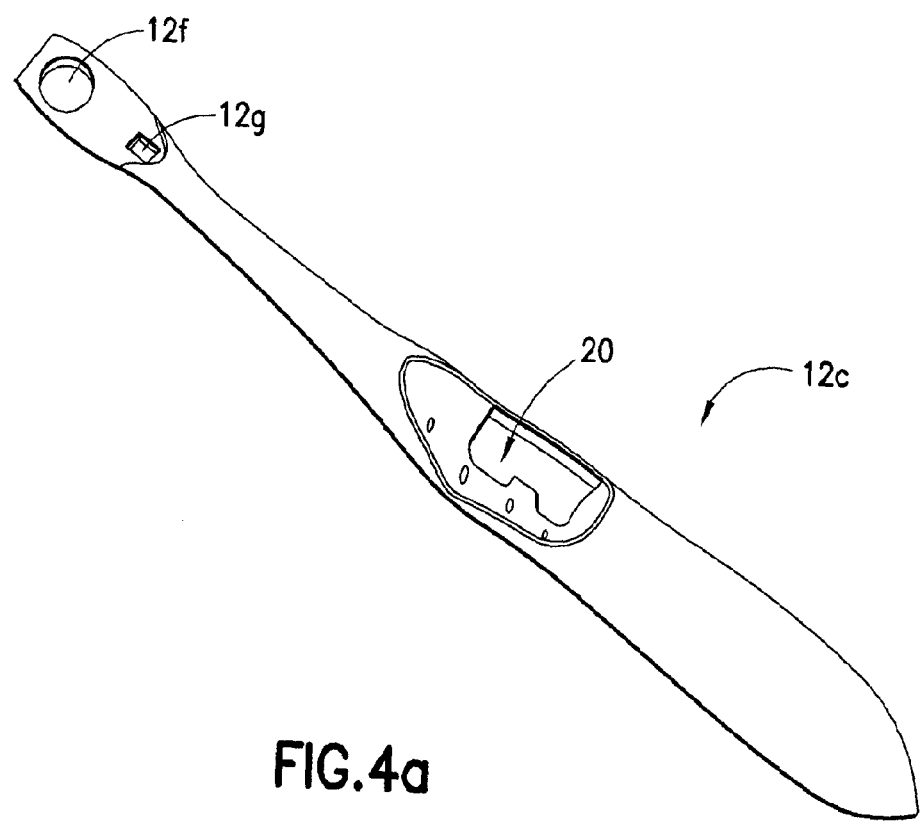
FIG. 4A is a perspective view of the exterior of the front housing cover portion of the direct drive electric toothbrush of FIG. 1 with the over-molded switch plate cover removed according to some embodiments of the invention.
Figure 4B:
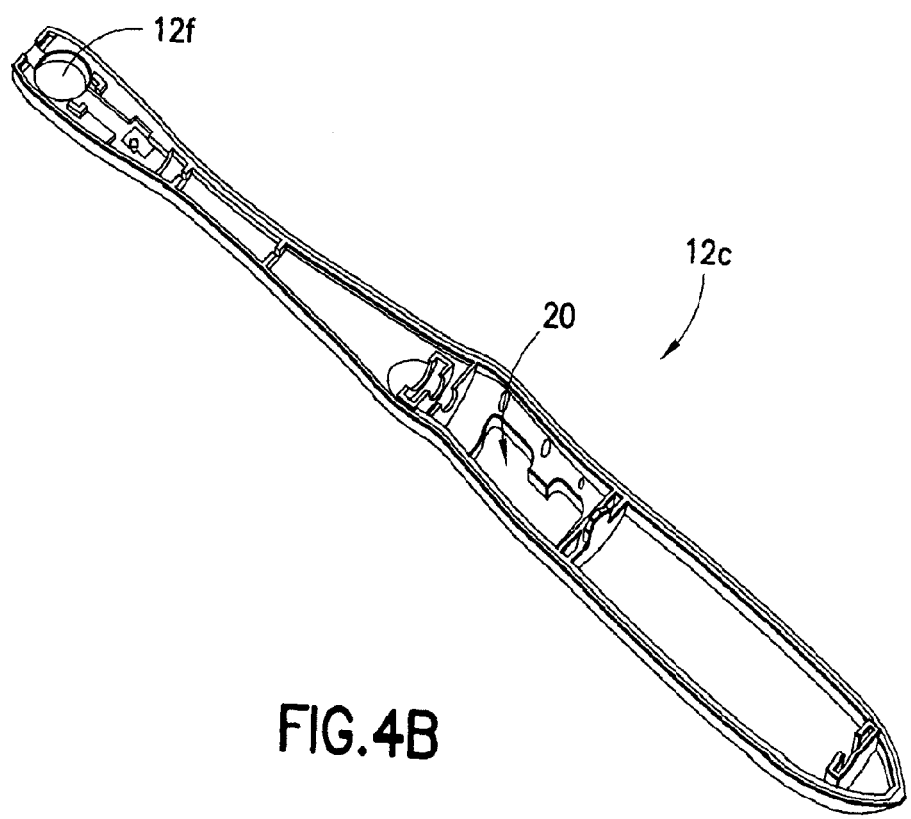
FIG. 4B is a perspective view of the interior of the front housing cover portion of the direct drive electric toothbrush of FIG. 1 with the over-molded switch plate cover removed according to some embodiments of the invention.
Figure 5A:
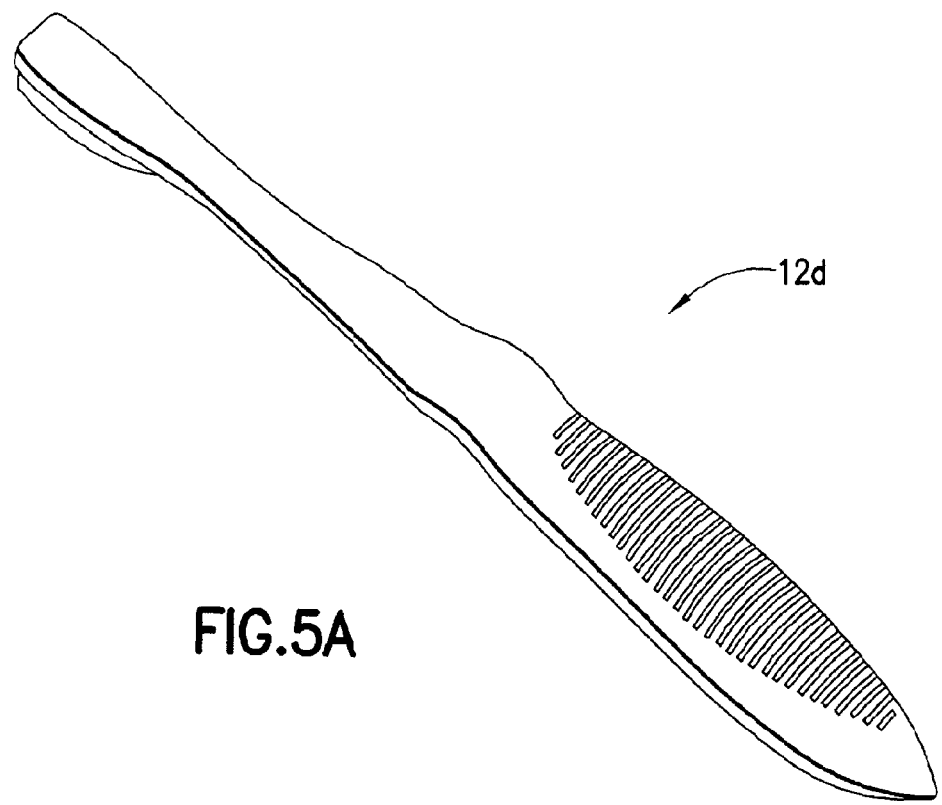
FIG. 5A is a perspective view of the exterior of the back housing cover portion of the direct drive electric toothbrush of FIG. 1 according to some embodiments of the invention.
Figure 5B:
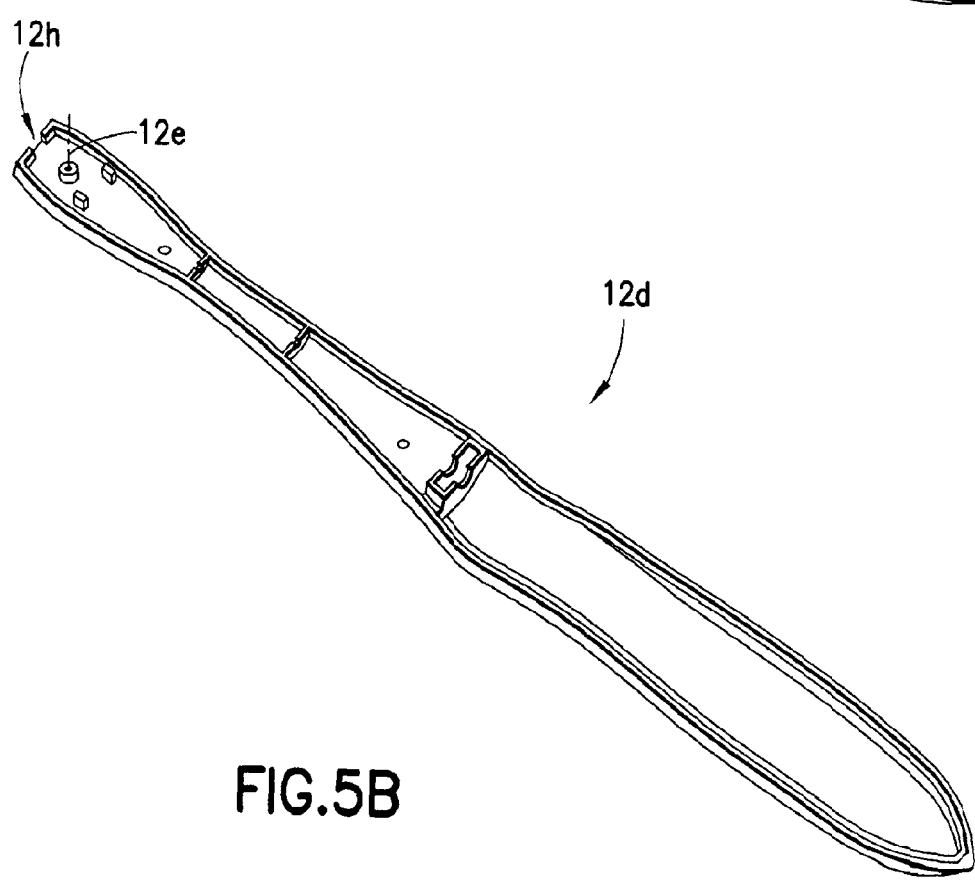
FIG. 5B is a perspective view of the interior of the back housing cover portion of the direct drive electric toothbrush of FIG. 1 according to some embodiments of the invention.

In accordance with some embodiments of the direct drive electric toothbrush of the present invention, for example as illustrated in a schematic side view in FIG. 1, the direct drive electric toothbrush is generally designated 10 and comprises a body housing generally designated 12 having a handle portion generally designated 12a, a head portion generally designated 12b and a neck portion generally designated 14 extending between the handle portion 12a and the head portion 12b. The body housing 12 has a front housing cover generally designated 12c and a back housing cover generally designated 12d. The front housing cover 12c is illustrated in a perspective view in FIG. 4A showing the exterior surface of the front cover and is illustrated in FIG. 4B in a perspective view showing the interior of the front housing cover 12c. The back housing cover 12d is illustrated in perspective view in FIG. 5A showing the exterior surface of the back housing cover and is illustrated in FIG. 5B in a perspective view showing the interior of the back housing cover. The shape of the front and rear housing cover portions is such that a hollow interior region is defined to mount and receive the various components of the direct drive electric toothbrush 10.

Figure 8A:
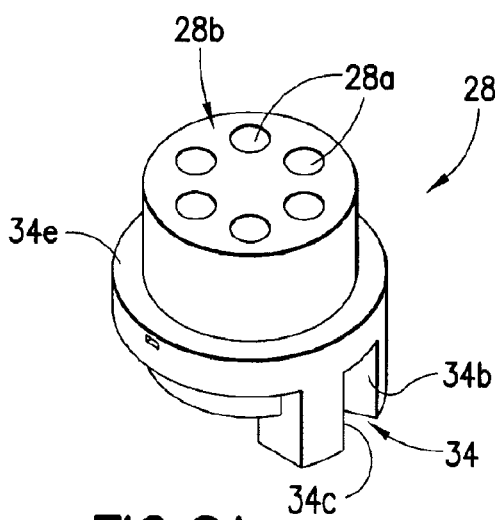
FIG. 8A is a perspective view of the front of the oscillating head bristle plate showing six apertures for receiving bristles according to some embodiments of the invention.
Figure 8B:
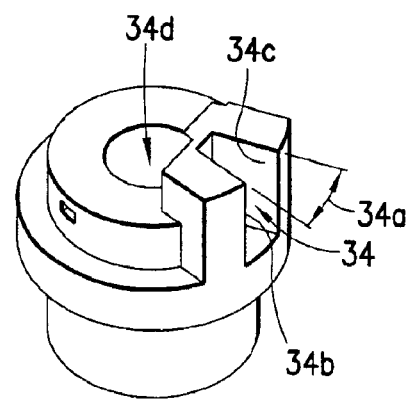
FIG. 8B is a perspective view of the back of the oscillating head bristle plate showing the oscillating plate cavity for receiving the cam carried by the driveshaft according to some embodiments of the invention.

The head portion 12b carries a static or fixed bristle holder plate generally designated 22 having a plurality of bristles 24 extending from the surface 22a thereof forming tufts of bristles 26 in a desired pattern. The static bristle holder plate 22 may be detachable from the head 12b. The height of the bristles is variable and determined in accordance with the particular design requirements, brushing action, bristle material and other considerations well known to those skilled in the art. The head 12b also includes a movable oscillating head bristle holder generally designated 28 shown in perspective view in FIGS. 8A and 8B. The oscillating head bristle holder 28 has a number of apertures 28a in the top surface 28b for receiving a plurality of other bristles 30 forming tufts of other bristles 32 which are driven in an oscillating motion when power is supplied to the direct drive electric toothbrush of the present invention.

Figure 6A:
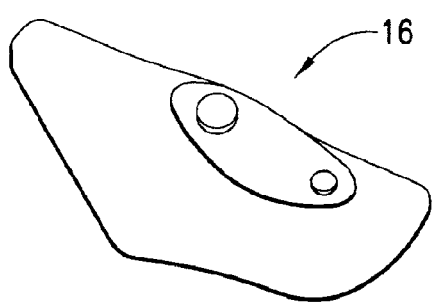
FIG. 6A is a perspective view of the exterior of the over-molded switch plate cover according to some embodiments of the invention.
Figure 6B:
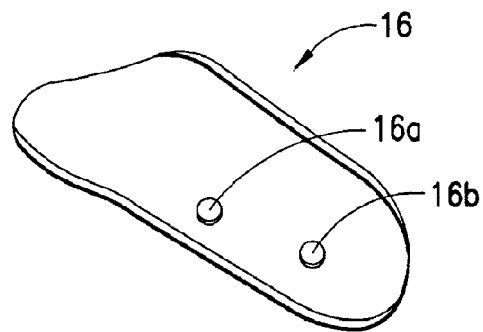
FIG. 6B is a perspective view of the interior of the over-molded switch plate cover according to some embodiments of the invention.
Figure 7A:
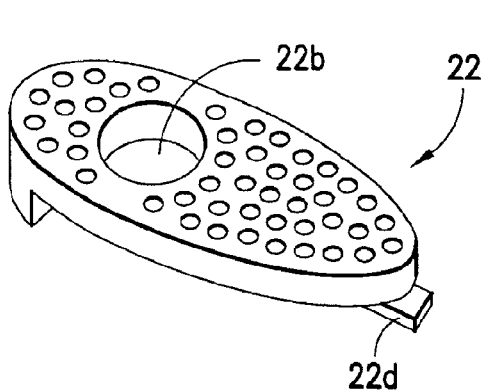
FIG. 7A is a perspective view of the front of a fixed bristle holder plate showing apertures for receiving bristles according to some embodiments of the invention.
Figure 7B:
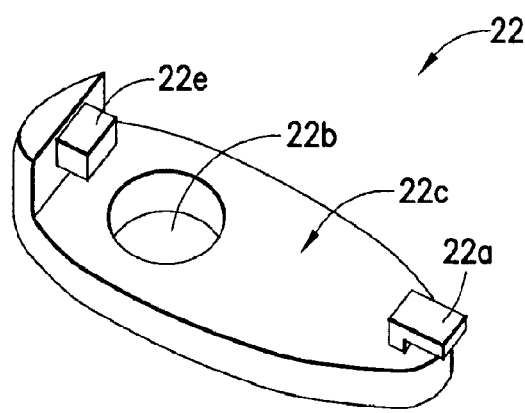
FIG. 7B is a perspective view of the back of a fixed bristle holder plate showing two lugs adapted to be received in apertures in the head portion of the front housing cover portion according to some embodiments of the invention.
Figure 17A:
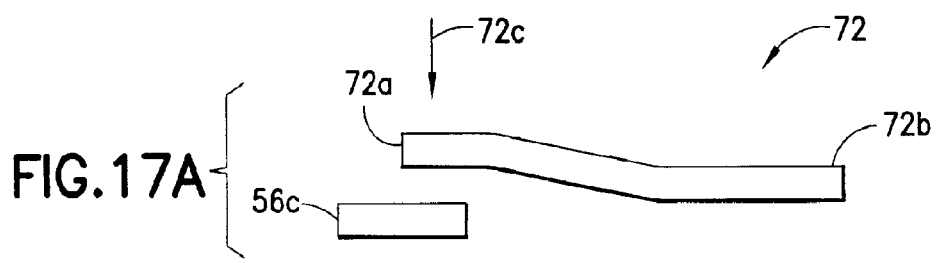
FIG. 17A shows a schematic representation of a "snap action" switch in its off state according to some embodiments of the invention.
Figure 17B:
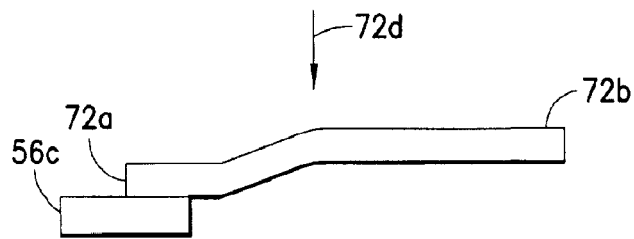
FIG. 17B shows a schematic representation of a "snap action" switch in its on position according to some embodiments of the invention.

In some embodiments of the invention, an over-molded switch plate cover generally designated 16 is sealingly attached to the surface of the front housing cover 12c to seal the switch access opening 20 for providing a waterproof covering for the front housing cover to prevent water or liquids from entering into the motor disposed in the hollow interior of the direct drive electric toothbrush in its assembled state. The over-molded switch plate cover 16 is made of a suitable flexible material such as an elastomer or plastic, to permit operation of the on/off switch to connect electrical power to the motor from the power source to operate the toothbrush. The on/off switch may be arranged as an electrically conductive "snap action" conductive strip that snaps closed to make contact with the motor housing and the power source when operated to the on state and snaps open to disconnect the motor housing from the power source when operated to the off state The exterior of the over-molded switch plate cover 16 is shown in a perspective view in FIG. 6A and the interior of the over-molded switch plate cover 16 is shown in a perspective view in FIG. 6B. Molded bosses 16a and 16b provide contact to the "snap action" conductive strip. A schematic representation of a "snap action" switch is shown in FIGS. 17A and 17B generally designated 72 wherein in FIG. 17A the switch 72 is shown in the "off" position. The switch is operated "on" by pushing down (indicated by the arrow 72c) on the end 72a to "snap" the end 72a from its first retention memory state into contact with a cooperating contact surface 56c. The opposite end 72b of the switch is fixed. The switch is operated "off" by pushing down (indicated by the arrow 72d) on the region near the end 72b to "snap" the end 72a to its second retention state and out of contact with the cooperating contact surface 56c. The design of the "snap action" switch is within the purview of those skilled in the art.

Figure 2:
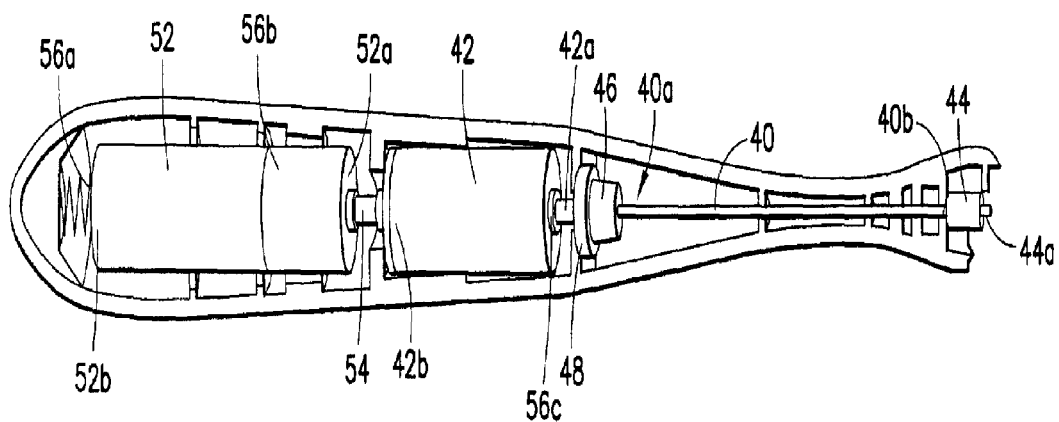
FIG. 2 shows the direct drive electric toothbrush with the front housing cover portion removed to reveal the interior structure and major drive components according to some embodiments of the invention.
Figure 3:
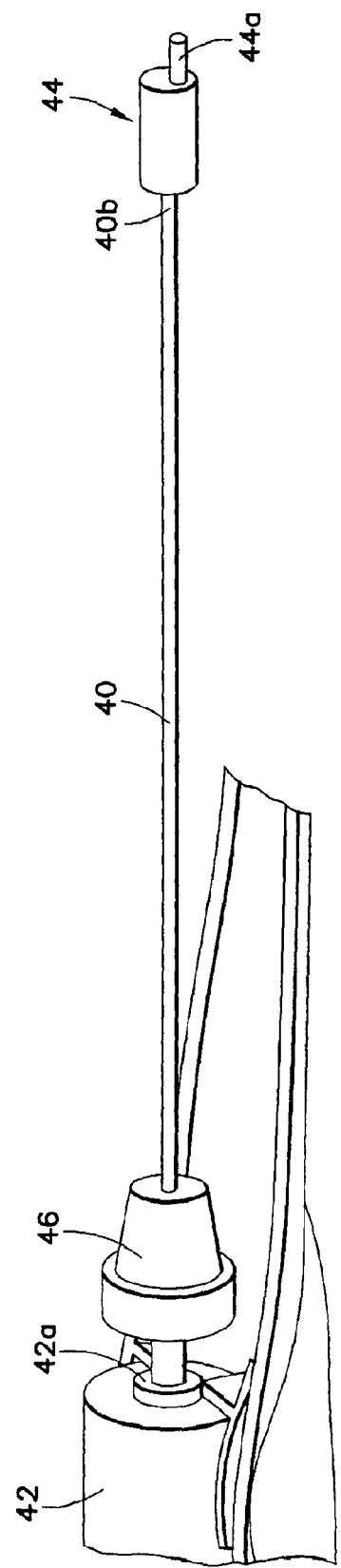
FIG. 3 shows the neck portion of the direct drive electric toothbrush with the drive shaft tilted out according to some embodiments of the invention.

In accordance with some embodiments of the invention the direct drive electric toothbrush 10 is illustrated by way of example in FIGS. 2 and 3 and is shown with the front housing cover 12c removed to reveal the interior structure and major drive components. An axially elongated drive shaft 40 extends through the neck portion 14 from the drive motor 42 disposed in the handle portion 12a to the cam 44 at the head portion 12b of the body 12. The drive shaft 40 may be of any suitable material, such as, for example, stainless steel, or other suitable material known to those skilled in the art. In some embodiments of the invention, the end 40a of the drive shaft 40 nearest the motor 42 is inserted or press fitted into a bore in one end of a coupler generally designated 38 in FIG. 13 and the opposite end of the coupler 38 is coupled or otherwise attached to the output drive shaft 42a of the motor 42 to directly drive the rotation of the drive shaft 40. The coupler 38 may be of any suitable material such as an elastomer material which provides flexibility in operation and facilitates assembly and also provides a mechanism for absorbing twisting shock of the motor drive shaft 42a in the event that the rotation motion of the drive shaft 40 becomes restricted or otherwise impeded or interfered with.

In some embodiments of the direct drive electric toothbrush 10 of the invention, the output drive shaft 42a of the motor 42 may pass through a seal 48 arranged to provide a seal between the area of the drive shaft 40 in the neck portion 14 and the motor 42 to prevent liquids or water from contacting the motor. The seal 48 may be of any suitable material and sized and shaped to seal the drive shaft 40 while allowing it to rotate. In other words the seal also functions as a bushing. The outer surface circumference of the seal 48 is sized and shaped to conform to the interior surface of the front housing cover 12c and rear housing cover 12d when the direct drive toothbrush is assembled to define the body 12.

In some embodiments of the invention, the end 40b of the drive shaft 40 nearest the head portion 12b is inserted or press fitted into a bore in one end of the cam 44. The cam 44 has at least one lobe 44a which is used to impart oscillatory motion to the oscillating head bristle plate holder 28. The material of the cam 44 may be of any suitable material; however, a plastic material presents less weight and is easier to manufacture through molding techniques that are well known to those skilled in the art.

Figure 12:
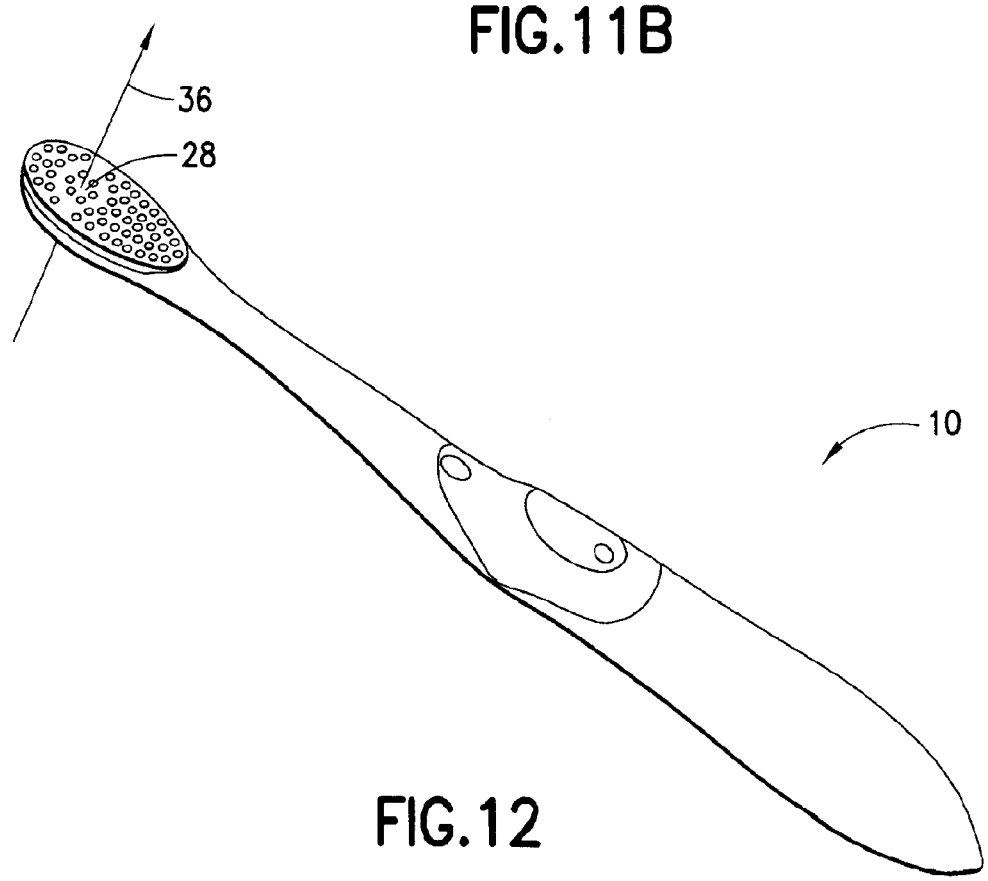
FIG. 12 is a perspective view of the front of the electric toothbrush with the bristles removed from the static bristle holder plate and the oscillating head bristle holder plate according to some embodiments of the invention.

An oscillating cavity generally designated 34 is located in the lower outer wall portion of the oscillating head bristle holder 28 which has a generally cylindrical shaped form factor. The oscillating cavity 34 is arranged for receiving the cam 44 and the side-to-side dimension indicated by the angle 34a of the oscillating cavity 34 is defined by the separation of a first side wall 34b and an oppositely disposed side wall 34c. The oscillating head bristle holder 28 has an opening 34d in its bottom surface which is sized to fit on a boss or post 12e located on the interior side of the back cover housing 12d so that the oscillating head bristle holder plate 28 can rotate about a pivot or rotation axis 36 which is substantially perpendicular to the longitudinal axis of the body 12 when the electric tooth brush is in its assembled condition as shown in a perspective view in FIG. 12. The oscillating head bristle holder 28 can be designed to rotate different angles in each direction from an at rest position by controlling the separation distance between the sidewalls 34b and 34c and the height of the cam lobe 44a. The at rest position is defined for the purpose of explanation as a center position in axially alignment with the drive shaft. The oscillating head bristle holder rotates in a first direction in response to the cam lobe 44a pushing on the sidewall 34b and in a second opposite direction in response to the cam lobe 44a pushing on the sidewall 34c as the cam 44 rotates as it is driven by the drive shaft 40. It should be apparent that the cam lobe height is greater for larger degrees of rotation because the separation of the sidewalls is greater than for lesser degrees of rotation which are driven by cams having lobes of correspondingly less height. The oscillating head bristle holder may rotate up to 90 degrees in each direction giving 180 degrees total movement. Typically, the total movement is less than 180 degrees and is dependent on the bristle material, cleaning efficacy to be obtained, surface to be cleaned and other considerations well known to those in the art. Generally movement of approximately 20 degrees in each direction, giving 40 degrees of total movement provides satisfactory cleaning performance in the direct drive electric toothbrush of the present invention.

When the front housing cover 12c and rear housing cover 12d are assembled, an aperture or opening 12f is in registry with the boss or post 12e and the oscillating head bristle holder 28 and is retained in place by the static or fixed holder plate 22 which has an opening 22b that is suitably dimensioned to fit over the top portion of the oscillating head bristle holder 28 but not over the circumferential peripheral collar 34e to retain the oscillating head bristle holder 28 in the head potion 12b so that it may rotate about the pivot post. The static or fixed bristle holder plate 22 includes a lug 22d and which is arranged to be received in a corresponding aperture 12g in the head portion 12b of the front housing cover 12c, and a lug 22e which is arranged to be received in a corresponding aperture 12h which is formed between the front and rear housing covers 12c and 12d when the body 12 is assembled. In some embodiments of the invention, the fixed or static bristle holder plate 22 is detachable so that the tufts of bristles held by the static bristle holder plate and the oscillating bristle holder respectively are replaceable.

Figure 11A:
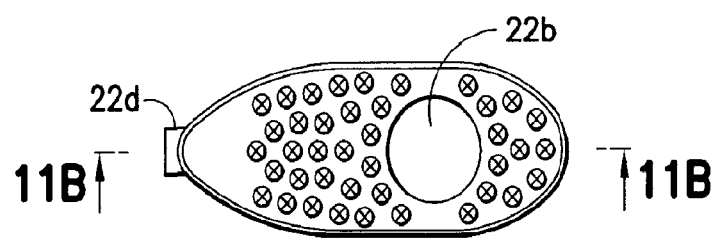
FIG. 11A is a top plan view showing tufts of bristles arranged to partially cover the front surface of the bristle holder plate according to some embodiments of the invention.
Figure 11B:
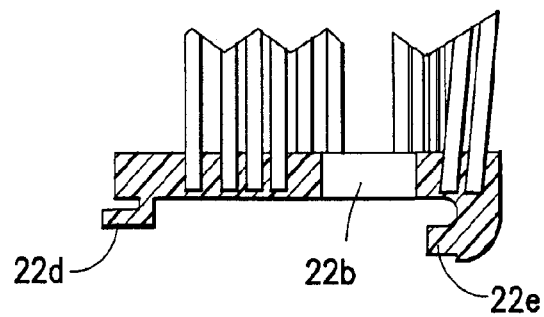
FIG. 11B is a cross-section view taken along the line 11B-11B of FIG. 11A showing the lugs and opening in which the oscillating head bristle carrier rotates according to some embodiments of the invention.

In some embodiments of the invention, the surface of the fixed or static bristle holder plate 22 is fully populated with tufts of bristles as shown in the top plan view in FIG. 9A to completely cover the surface. FIG. 9B shows a cross-section view along the line 9B-9B in FIG. 9A and shows the height pattern of the tufts of bristles and the opening 22b through which the tufts of bristles carried by the oscillating head bristle holder passes. In some embodiments of the invention, the surface of the fixed or static bristle holder plate 22 has fewer openings for receiving bristles so that the tufts of bristles as shown in the top plan view in FIG. 11A only partially cover the surface. FIG. 10B shows a cross-section view along the line 10B-10B in FIG. 10A and shows the height pattern of the tufts of bristles and the opening 22*b* through which the tufts of bristles carried by the oscillating head bristle holder passes.

In some embodiments of the invention the motor 42 is disposed in the handle portion 12*a* of the body 12 sandwiched in a mounting assembly 50 as illustrated in FIG. 15 comprising top motor mount 50*a* and a lower motor mount 50*b* to hold the motor in place and in substantially direct alignment with the drive shaft 40. The motor 42 may operate at different speeds to drive the oscillating head bristle holder with a corresponding different rate of oscillation. The motor 42 is axially elongated to provide a smaller diameter to fit within the hollow interior region of the handle portion so that the shape of the handle may be made ergonomically comfortable for a user. The motor 42 may also be of any suitable type to carry out the function of the invention. Generally the motor is a direct current (DC) voltage operated motor and is selected with size, weight and energy consumption considerations taken into account. In some embodiments of the invention, a suitable power source such as a DC voltage battery 52 is aligned with the motor 42 and is in electrical contact with the positive end 42*b* of the motor 42 through an electrical contact 54, which is in contact with the positive end 52*a* of the battery 52 when the battery is disposed in the battery compartment of in the handle portion 12*a* of the direct drive electric toothbrush 10. A spring arrangement 56 includes a coiled spring end portion 56*a* in contact with the negative end 52*b* of the battery 52 for urging the positive end 52*a* into contact with the electrical contact 54 and holding the battery in place. A leg extends from the coiled spring end portion terminating at a contact 56*c* in the region of the motor 42 so that the over-molded switch plate 16 completes the electrical circuit when the over-molded switch plate is operated and disconnects the electrical circuit when the over-molded switch plate cover is again operated a second time thereby toggling the motor on and off. The DC voltage battery is selected in accordance with the specific motor used. In some embodiments of the invention, the motor is operated from a 1.5 volt DC power source such as for example a AA battery. In some embodiments of the invention, the power source is a rechargeable battery.

Figure 16:
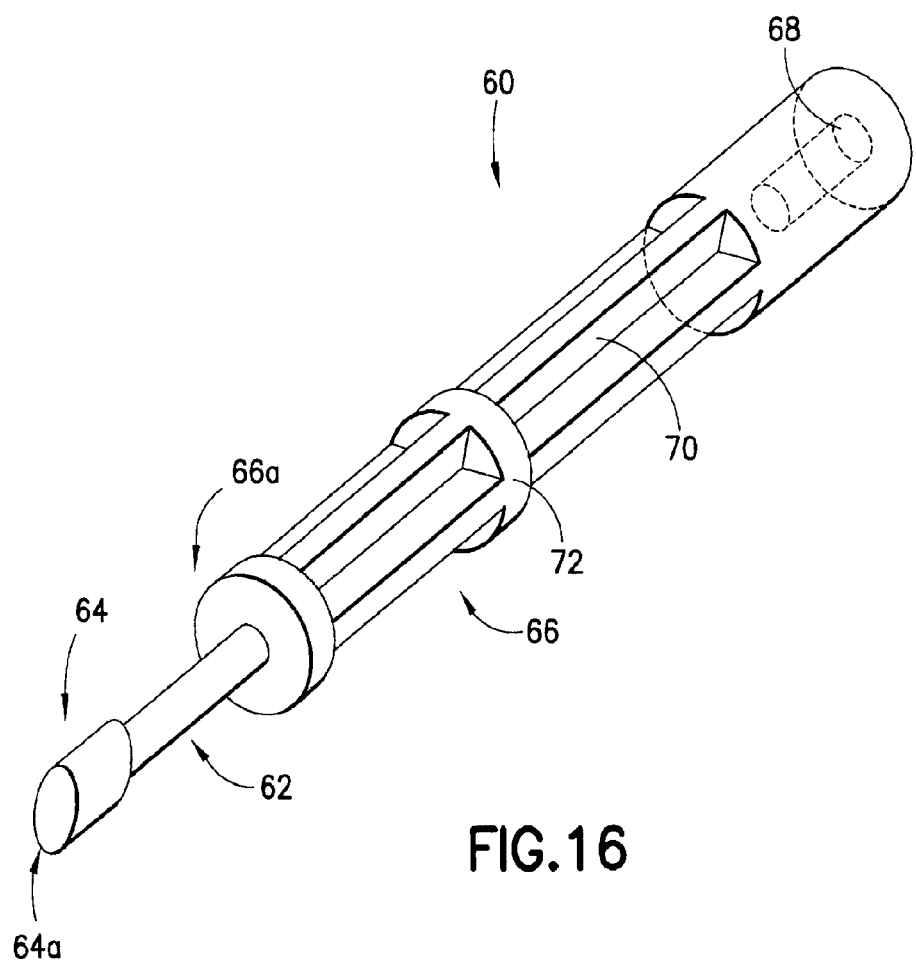
FIG. 16 is a perspective view of an alternate embodiment of a drive shaft that may be utilized with the direct drive electric toothbrush according to some embodiments of the invention.

In accordance with some embodiments of the invention, a perspective view of an alternate embodiment of a drive shaft that may be utilized with the direct drive electric toothbrush embodying the present invention is shown in FIG. 16 and is generally designated 60. The driveshaft 60 combines a metal drive shaft section 62, a plastic driving cam 64 having at least one lobe 64*a*, and a cylindrical bearing 66 into a simple, inexpensive combination. In this embodiment, the drive shaft portion 62 is inserted into the head-end 66*a* of the bearing 66, and may run the length of the bearing 66 for a direct connection to the output drive shaft 42*a* of the motor 42. Alternatively, the drive shaft portion 66 may run less than the full length of the bearing 66, in which case the motor-end of the bearing includes a way for attaching to the motor drive shaft 42*a* using a cored out section 68 at the end of the bearing nearest the motor. The cored out section 68 is arranged for a press fit onto the drive shaft 42*a* of the motor 42. The length of the metal drive shaft 62 extending from the head-end 66*a* of the bearing 66 is minimized to reduce the potential for flexing and premature breakage.

Portions of the bearing 66 may be fabricated so as to have a cruciform cross section 70 for purposes of structural strength and material savings. Portions of the bearing 66 may also retain round cross sections 72 to prevent water from contacting the motor when used in conjunction with a suitable seal of proper dimension, configuration and material for sealing. The diameter of the bearing may vary as a function of the dimensions of the hollow interior cavity formed between the front housing cover 12*c* and rear housing cover 12*d*. The bearing 66, cam 64, and any other component parts of the electric brush may be made from plastics such as DuPont Delrin® 100P.

The parts of the direct drive electric toothbrush embodying the present invention are not intended to be limited to the materials described herein and may be made of plastics including standard engineering resins, metal, or other materials consistent with the intended function of the parts, the proper selection of which material is within the purview of those skilled in the art.

Figure 18:
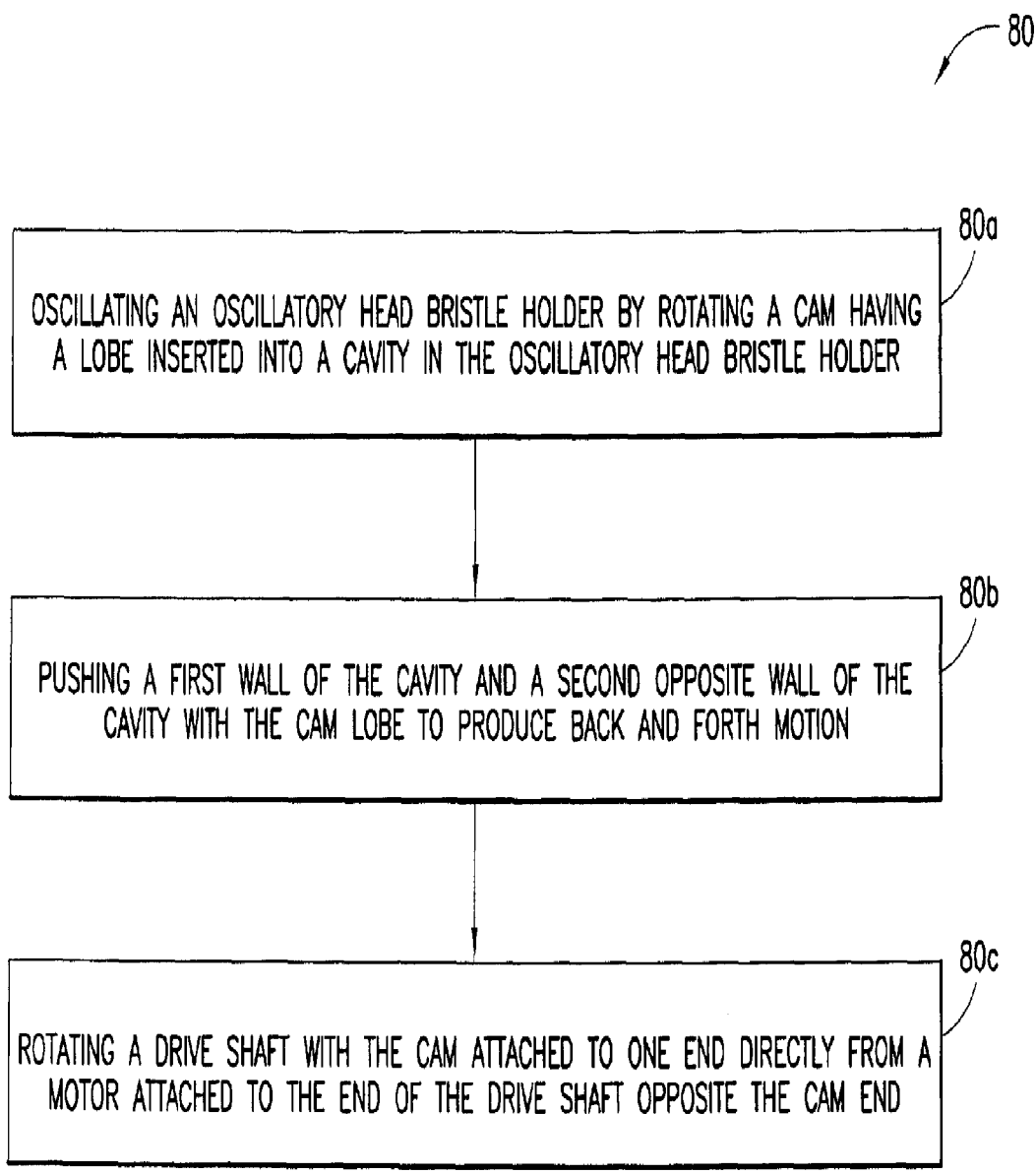
FIG. 18 shows a flowchart of the basic steps of the method for oscillating a bristle head according to some embodiments of the invention.

FIG. 18 shows a flowchart generally designated 80 having the basic steps or actions 80*a*, 80*b*, 80*c* for implementing the inventive method for oscillating a bristle head according to some embodiments of the invention, for example in an electric toothbrush, comprising oscillating an oscillating head bristle holder by rotating a cam having a lobe inserted into a cavity in the oscillatory head bristle holder (step 80*a*), pushing a first wall of the cavity and a second opposite wall of the cavity with the cam lobe to produce a back and forth oscillatory motion (step 80*b*), and rotating a drive shaft with the cam attached to one end directly from a motor attached to the end of the drive shaft opposite the cam end (step 80*c*). The scope of the invention is not intended to be limited to the order in which the steps or actions in FIG. 17 are performed. Further, the scope of the invention is not intended to be limited to any particular implementation using technology now known or developed in the future for directly driving the oscillatory bristle head holder in an electric toothbrush or other cleaning apparatus.

Likewise, the use of the direct drive electric toothbrush embodying the present invention is not intended to be limited to the cleaning of human teeth and may be used for cleaning any teeth including natural, artificial, or animal teeth in veterinary applications. Further, as is evident from the description, the principles of the direct drive electric toothbrush embodying the invention may be applied for use in cleaning generally.

It is to be understood that the arrangements shown and described above and in the attachments are only illustrative of the application of the principles of the present invention. Numerous modifications and alternative arrangements may be devised by those skilled in the art without departing from the scope of the present invention, and the appended claims are intended to cover such modifications and arrangements.

It is also contemplated that the present invention not be limited to the examples of embodiments described herein and includes any and all combinations that may be readily inferred directly or indirectly from the drawing figures and the written description whether or not expressly set forth herein.

What is claimed is:
1. An apparatus, comprising:
   a housing having a desired shape and defining a hollow interior region therein, and having a handle portion, a head portion and a neck portion extending between the handle portion and the head portion;
   a motor arranged with a motor output shaft disposed within said housing;
   a drive shaft having a first end and a second end, and arranged to be operatively coupled at said first end to said motor output shaft for rotation thereby;
   a cam comprising a cam lobe and operatively connected to said drive shaft at said second end of said drive shaft, wherein the cam and the cam lobe each have a longitudinal axis, and each longitudinal axis is positioned parallel to the other;

a static bristle holder plate connected to said housing and having a surface with a collection of static bristles extending there from; and a movable oscillatory head bristle holder plate retained by said static bristle holder plate, wherein the movable oscillatory head bristle holder plate comprises a top surface with a collection of movable bristles extending there from, a cylindrical sidewall extending perpendicularly from the top surface, and a circumferential peripheral collar positioned concentrically around the cylindrical sidewall, wherein said static bristle holder plate being arranged and configured to retain said movable oscillatory head bristle holder plate such that the surface of said static bristle holder plate and the top surface of said movable oscillatory head bristle holder plate lie in a common plane and the circumferential peripheral collar of said movable oscillatory head bristle holder plate is sandwiched between said static bristle holder plate and said head portion of the housing, wherein said movable oscillatory head bristle holder plate comprises a side peripheral wall and a cavity defined therein, and wherein the cam lobe is positioned at least partially within said cavity of said movable oscillatory head bristle holder plate so that rotational movement of the cam causes oscillatory movement of said movable oscillatory head bristle holder plate.

2. The apparatus as defined in claim 1, wherein the drive shaft is a straight drive shaft that extends the length of the housing from the motor output shaft to the cam.

3. The apparatus as defined in claim 1, wherein the cam pushes the movable oscillatory head bristle holder plate back and forth up to 20 degrees in each direction from an at rest position.

4. The apparatus as defined in claim 1, wherein the collection of static bristles are attached to said static bristle holder plate.

5. The apparatus as defined in claim 1, wherein the collection of movable bristles are attached to said movable oscillatory head bristle holder plate.

6. The apparatus as defined in claim 1, wherein the cam is made of a material selected from the group consisting of metals and plastic.

7. The apparatus as defined in claim 1, wherein the drive shaft comprises a cylindrical bearing positioned between the first end and the second end of the drive shaft, and a metal portion extending from the bearing towards the second end of the drive shaft.

8. The apparatus as defined in claim 7, wherein the bearing has one or more cruciform cross sectional regions located between one or more rounded cross sectional regions.

9. The apparatus as defined in claim 7, wherein the cylindrical bearing is arranged to connect to the motor output shaft.

10. The apparatus as defined in claim 9, wherein the bearing further comprises a cored out region of the bearing configured to be press fitted directly onto the motor output shaft.

11. The apparatus as defined in claim 7, wherein the hollow interior of the housing comprises a plurality of inner diameters, and wherein the diameter of the cylindrical bearing varies as a function of the inner diameters of the hollow interior of the housing.

12. An electric toothbrush, comprising:
an axially elongated body, comprising:
a handle defining a hollow interior region shaped and configured to hold a motor disposed therein, said motor having a motor output shaft;

a head comprising a static bristle holder plate having tufts of bristles disposed on a surface thereon and connected to said head;

a movable oscillatory head bristle holder plate with other tufts of bristles disposed on a top surface thereon and having a cylindrical sidewall extending perpendicularly from the top surface, and a circumferential peripheral collar positioned concentrically around the cylindrical sidewall, said movable oscillatory head bristle holder being arranged and located with respect to said static bristle holder plate so that said tufts of other bristles of said movable oscillatory head bristle holder are at least partially surrounded by said tufts of bristles of said fixed portion of said static bristle holder plate, said static bristle holder plate being arranged and configured to retain said movable oscillatory head bristle holder plate such that the surface of said static bristle holder plate and the top surface of said movable oscillatory head bristle holder plate lie in a common plane and the circumferential peripheral collar of said movable oscillatory head bristle holder plate is sandwiched between said static bristle holder plate and said head;

a neck extending between said handle and said head;

a drive shaft having a first end, a second end and a longitudinal axis and, wherein said first end of said drive shaft is operatively connected to said motor output shaft;

a cam comprising a cam lobe and operatively connected to said drive shaft at said second end of said drive shaft, wherein the cam and the cam lobe each have a longitudinal axis, and each longitudinal axis of the cam and the cam lobe is positioned parallel to the other;

wherein said movable oscillatory head bristle holder plate comprises a side peripheral wall and a cavity defined therein, and wherein said cam lobe is positioned at least partially within said cavity of said movable oscillatory head bristle holder plate so that rotational movement of the cam causes oscillatory movement of said movable oscillatory head bristle holder plate.

13. The electric toothbrush as defined in claim 12 wherein said static bristle holder plate is releasably attached to said head.

14. Method, comprising:
oscillating an oscillating head bristle holder having a top surface with a collection of movable bristles extending there from, a cylindrical sidewall extending perpendicularly from the top surface, a circumferential peripheral collar positioned concentrically around the cylindrical sidewall, a side peripheral wall and a cavity defined in the side peripheral wall by rotating a cam having a cam lobe inserted into the cavity in the oscillatory head bristle holder, wherein the cam and the cam lobe each have a longitudinal axis and each longitudinal axis is positioned parallel to each other, and wherein the cavity comprises a first side wall and an oppositely disposed second side wall;

retaining said oscillating head bristle holder between a static bristle holder plate and a head portion such that the circumferential peripheral collar of said oscillating head bristle holder is sandwiched between said static bristle holder plate and said head portion;

pushing the first side wall of the cavity and the second side wall of the cavity with the cam lobe to produce a back and forth oscillatory motion in the oscillating head bristle holder, and rotating a drive shaft with the cam attached to one end directly from a motor attached to an end of the drive shaft opposite the end attached to the cam.

* * * * *